(12) United States Patent
Busseret et al.

(10) Patent No.: US 11,009,505 B2
(45) Date of Patent: May 18, 2021

(54) REAGENT DILUENT

(71) Applicant: BIOMERIEUX, Marcy l'Etoile (FR)

(72) Inventors: Sandrine Busseret, Lyons (FR);
Florence Bettsworth, Dommartin (FR);
Jérôme Martinez, Lyons (FR)

(73) Assignee: BIOMERIEUX, Marcy l'Etoile (FR)

( * ) Notice: Subject to any disclaimer, the term of this patent is extended or adjusted under 35 U.S.C. 154(b) by 257 days.

(21) Appl. No.: 16/063,524

(22) PCT Filed: Dec. 20, 2016

(86) PCT No.: PCT/FR2016/053566
§ 371 (c)(1),
(2) Date: Jun. 18, 2018

(87) PCT Pub. No.: WO2017/109376
PCT Pub. Date: Jun. 29, 2017

(65) Prior Publication Data
US 2019/0204308 A1 Jul. 4, 2019

(30) Foreign Application Priority Data
Dec. 21, 2015 (FR) ..................................... 1562932

(51) Int. Cl.
| | |
|---|---|
| *G01N 33/543* | (2006.01) |
| *G01N 33/68* | (2006.01) |
| *C08F 220/60* | (2006.01) |
| *C08L 33/02* | (2006.01) |
| *C08L 43/02* | (2006.01) |
| *G01N 33/53* | (2006.01) |

(52) U.S. Cl.
CPC ....... *G01N 33/5436* (2013.01); *C08F 220/60* (2013.01); *C08L 33/02* (2013.01); *C08L 43/02* (2013.01); *G01N 33/53* (2013.01); *G01N 33/68* (2013.01)

(58) Field of Classification Search
CPC ........ C08L 33/02; C08L 43/02; C08F 220/60; G01N 33/53; G01N 33/5436; G01N 33/68
See application file for complete search history.

(56) References Cited

U.S. PATENT DOCUMENTS

| | | | |
|---|---|---|---|
| 6,492,501 B1 | 12/2002 | Popot et al. |
| 8,207,263 B2 | 6/2012 | Popot et al. |
| 8,674,044 B2 | 3/2014 | Popot et al. |
| 2009/0036625 A1 | 2/2009 | Chang et al. |
| 2011/0014189 A1 | 1/2011 | Soula et al. |

FOREIGN PATENT DOCUMENTS

| | | |
|---|---|---|
| EP | 1314982 A1 | 5/2003 |
| WO | 98/27434 A1 | 6/1998 |
| WO | 2008/058963 A1 | 5/2008 |
| WO | 2010/073119 A1 | 7/2010 |

OTHER PUBLICATIONS

English translation of the International Preliminary Report on Patentability issued for PCT/FR2016/053566 dated Jun. 26, 2018.*
A printout retrieved from https://www.nofamerica.com/store/index.php?dispatch=categories.view&category_id=147 on Dec. 14, 2020.*
Feb. 24, 2017 International Search Report issued in International Patent Application No. PCT/FR2016/053566.
J.-L. Popot et al. "Amphipols From A to Z". Annual Review of Biophysics, vol. 40, No. 1, Jun. 9, 2011, pp. 379-408.
Martin Picard et al. "Protective and Inhibitory Effects of Various Types of Amphipols on the Ca 2+-Atpase From Sarcoplasmic Reticulum: A Comparative Study". Biochemistry, vol. 45, No. 6, Feb. 1, 2006, pp. 1861-1869.
Kazuhiko Ishihara et al. "Why Do Phospholipid Polymers Reduce Protein Adsorption?". Journal of Biomedical Materials Research, Wiley, NY, US, vol. 39, No. 2, Jan. 1, 1998, pp. 323-330.
Shujiro Sakaki et al. "Stabilization of an Antibody Conjugated With Enzyme by 2-Methacryloyloxyethyl Phosphorylcholine Copolymer in Enzyme-Linked Immunosorbent Assay". Journal of Biomedical Materials Research, vol. 47, 1999, pp. 523-528.
Shujirou Sakaki et al. "Water-Soluble 2-Methacryloyloxyethyl Phosphorylcholine Copolymer as a Novel Synthetic Blocking Reagent in Immunoassay System". Polymer Journal, vol. 32, No. 8, 2000, pp. 637-641.
Manuela Zoonens et al. "Amphipols for Each Season". J. Membr. Biol., Oct. 2014, vol. 247, pp. 759-796.
Manuela Zoonens et al. "Chapter 7 Amphipols: A General Introduction and Some Protocols". Springer Science+Business Media, New York, 2014, pp. 173-203.
N. Nakabayashi et al. "Copolymers of 2-Methacryloyloxyethyl Phosphorylcholine (MPC) as Biomaterials". Bio-Medical Materials and Engineering, vol. 14, 2004, pp. 345-354.
Joanna K. Nagy et al. "Use of Amphipathic Polymers to Deliver a Membrane Protein to Lipid Bilayers". FEBS Letters, vol. 501, 2001, pp. 115-120.
"MPC Biocompatible Material: The Structure of Biolipidure®". Life Science Products, NOF Corporation, <https://www.nof.co.jp/english/business/life/product01b.html> (2008).

* cited by examiner

*Primary Examiner* — Galina M. Yakovleva
(74) *Attorney, Agent, or Firm* — Oliff PLC

(57) ABSTRACT

An immunoassay composition includes at least (i) an amphipol and (ii) a (meth)acrylate monomer-based amphoteric copolymer, some of said monomers including a phosphorylcholine group. The composition is useful in particular as a stabilizer and/or blocking agent.

12 Claims, No Drawings

REAGENT DILUENT

The present invention relates to the field of diagnostics or prognosis. In particular, it relates to compositions useful for carrying out immunoassays, in particular as a stabilizer and/or a blocking agent.

STATE OF THE ART

Immunoassays are commonly used in the fields of clinical, food, pharmaceutical and chemical analyses. Thus, their purpose is to determine the presence of one or more analytes in samples that may contain them. Immunoassay is a test that is widely known to persons skilled in the art, which involves specific interactions between the analyte to be detected and one or more partner(s) that bind to this analyte. By way of example of said immunoassays, methods such as ELISA (Enzyme Linked Immuno Sorbent Assay), ELFA (Enzyme Linked Fluorescent Assay) and RIA (Radio Immuno Assay) may be mentioned, which can function according to the "sandwich" principle, or also according to the "competition" principle, and methods of immunodetection such as immunohistochemistry, immunocytochemistry, immunofluorescence, Western blot and dot blot. The "competition" methods are usually used for small molecules such as haptens, and the "sandwich" methods are used for the other analytes.

Immunoassays comprise contacting the sample that may contain an analyte with at least one labelled binding partner or a reagent that competes with the labelled analyte. Said binding partner or competitive reagent is for example formed from an antibody conjugated with a label that is able to deliver a signal. These reagents can be dissolved and stored in a diluent before being used in the immunoassay.

Regardless of the type of interactions detected, the adsorption on the solid matrix, on the binding partners or on the competitive reagent, of reagents that need not attach to them directly, can contribute to the generation of background noise. It is therefore essential to reduce these non-specific interactions in order to reduce the background noise as much as possible.

A blocking agent or saturating agent, which has the function of saturating the sites after adsorption, is used for this.

The diluents for immunoassay reagents can thus comprise blocking agents and/or stabilizers, on the one hand for stabilizing the reagents (conjugates, labels) and on the other hand for reducing the non-specific interactions of the reagent or reagents, for example with the solid matrix, the binding partners and/or a competitive reagent.

These blocking agents are preferably selected from proteins of animal or human origin, and in particular animal sera, skimmed milk, in particular in powder form, hydrolyzed or non-hydrolyzed caseins, bovine and human albumin, and gelatins.

These products of biological origin, and in particular of animal or human origin, have the drawback that their composition varies from batch to batch. In fact, for animal sera, their composition can vary depending on the species, breed, sex, as well as their feed (seasonal variation). For purified proteins, such as bovine albumin for example, the quality of these albumins varies according to the method of purification used, which depends on the supplier. Contamination, such as the presence of proteases, of bovine immunoglobulins or other molecules in greater or smaller quantities, accounts for the variations in background noise. These raw materials of human or animal origin maintain their stabilizing power, but the blocking power varies from batch to batch. Moreover, they must be used in accordance with the safety standards relating to biological risks, and there are also constraints in terms of supply and storage of the source products and handling thereof. Consequently, to overcome these drawbacks it would be advantageous to use synthetic stabilizers and/or blocking agents, useful in compositions for immunoassays, and in particular in diluents for reagents for immunoassays, such as labelled antibodies.

Amphoteric copolymers of 2-methacryloyloxyethyl phosphorylcholine are described as stabilizers and/or blocking agents in immunoassays of the ELISA type (Sakaki et al., 1999 J.Biomed.Mater.Res., 47, 523; Sakaki et al., 2,000, Polymer Journal, Vol. 32, No. 8, pp 637-641). Copolymers of 2-methacryloyloxyethyl phosphorylcholine are marketed by the company NOF Corporation under the trade name Biolipidure™ or Lipidure®. They are offered as an alternative to bovine albumin in particular for reducing non-specific interactions and/or for stabilizing labelled antibodies (EP1314982 A).

Patent applications WO 98/27434 and WO2008/058963 describe the use of amphiphilic polymers as solvent and stabilizer of membrane proteins or in vectoring applications. The use of these compounds, of the amphipol family, as stabilizers of therapeutic antibodies was also described in application WO2010/073119.

The applicant has now demonstrated that a composition comprising the combination of an amphipol and an amphoteric (meth)acrylate copolymer comprising at least one phosphorylcholine group can be used advantageously as a reagent stabilizer and/or blocking agent, in particular as a replacement for certain stabilizers and/or blocking agents of animal origin conventionally used.

Furthermore, quite surprisingly, the applicant demonstrated that the use of these compositions according to the invention in an immunoassay makes it possible to reduce the background noise signal appreciably, thus helping to increase the sensitivity of the assay, while maintaining the stability of the reagents over time.

SUMMARY

Thus, the present invention relates to a composition for immunoassay, comprising at least (i) an amphipol and (ii) an amphoteric copolymer based on (meth)acrylate monomers, a part of these monomers comprising a phosphorylcholine group.

In particular, the amphipol can be an amphiphilic polymer comprising a homopolymer or copolymer of maleic anhydride or of polyacrylate on which at least one hydrophobic group and a hydrophilic group are grafted, and having an average molecular weight comprised between 1,000 and 100,000, preferably between 4,000 and 70,000 g·mol$^{-1}$.

In a specific embodiment, the amphipol is selected from poly(maleic anhydride-alt-1-octadecene)s, poly(maleic anhydride-alt-1-tetradecene)s, poly(maleic anhydride-alt-1-decene)s, substituted with a hydrophilic group, for example an alkylated ammonium, and in particular 3-(dimethylamino)-1-propylamine.

In another specific embodiment, optionally combined with the preceding specific embodiments, the composition according to the invention is characterized in that the amphoteric copolymer is an amphoteric copolymer based on a monomer of 2-methacryloyloxyethyl phosphorylcholine (MPC) and of another methacrylate monomer functionalized with a hydrophobic group, an anionic group, a cationic group or a group allowing the formation one or more hydrogen bonds.

In a specific embodiment, the amphoteric copolymer is an amphoteric copolymer based on MPC and functionalized methacrylate with a hydrophobic group selected from
- linear or branched $C_4$ to $C_{30}$ alkyls;
- linear or branched $C_4$ to $C_{30}$ alkyls comprising at least one cycloalkyl;
- $C_4$ to $C_{30}$ hydrocarbon-containing chains comprising at least one double bond;
- $C_4$ to $C_{30}$ hydrocarbon-containing chains comprising at least one triple bond; or,
- $C_4$ to $C_{30}$ hydrocarbon-containing chains comprising at least one aromatic ring.

For example, they are Biolipidures™ or Lipidure®, for example Biolipidure™ 206 marketed in particular by the company NOF Corporation.

The invention also relates to an aqueous solution comprising the compositions according to the invention and at least one immunoassay reagent. In particular, in a preferred embodiment, the aqueous solution according to the invention is characterized in that it does not comprise a stabilizer and/or blocking agent of human or animal origin, for example selected from animal sera, skimmed milk, in particular powdered skimmed milk, hydrolyzed or non-hydrolyzed caseins, bovine or human albumin, and gelatins.

The invention further relates to immunoassay kits comprising at least one aqueous solution according to the invention, and at least one binding partner to an analyte to be detected or quantified by immunoassay and, if applicable, the compounds necessary for demonstrating a specific interaction between the binding partner or partners and the analyte.

The compositions and aqueous solutions according to the invention are useful in particular for reducing the non-specific interaction between
i. at least one binding partner intended to detect or quantify an analyte in a biological sample that may contain it, for example a labelled binding partner, and
ii. a solid phase.

They are also useful for reducing the non-specific interaction between
i. an immunoassay positive control, an immunoassay standard and/or an immunoassay adjuster, and
ii. a solid phase.

Finally, the invention relates to an immunoassay method for determining the presence or for quantification of a target analyte, in a biological sample that may contain it, comprising contacting said sample with at least two binding partners to said analyte, P1 and P2, sequentially or simultaneously, one of the two partners P2 being labelled to show the presence of said analyte, if it is present, the other partner P1 preferably being immobilized on a solid phase, and said labelled partner P2 being contained in at least one composition or aqueous solution according to the invention, to form if applicable a P1/analyte/P2 complex, detection of the presence of said complex formed allowing conclusions to be drawn concerning the presence or the quantity of analyte in the sample.

It also relates to an immunoassay method for determining the presence or for quantification of a target analyte, in a biological sample that may contain it, comprising contacting said sample with at least one binding partner P1 to said analyte and a reagent R1 that competes with the analyte, said binding partner P1 preferably being immobilized on a solid phase, said reagent R1 being labelled to show indirectly the presence of said analyte, and said reagent R1 being contained in at least one composition or aqueous solution according to the invention, to form a P1/R1 complex, detection of the presence of said complex formed allowing conclusions to be drawn indirectly concerning the absence or the quantity of analyte in the sample.

DETAILED DESCRIPTION

The applicant has therefore developed, against all expectations, immunoassay compositions making it possible to replace the macromolecules of animal origin conventionally used in diluents for immunoassay reagents.

The immunoassay compositions according to the invention comprise (i) an amphipol and (ii) an amphoteric copolymer based on (meth)acrylate monomers, a part of these monomers comprising a phosphorylcholine group or more generally a group of formula (III) described hereunder, for example a part of these monomers being the monomer of MPC (2-Methacryloyloxylethyl-PhosphorylCholine).

The Amphipols

Within the meaning of the invention, the term "amphipol" refers to the family of short, flexible amphiphilic polymers in particular described in the reviews by Zoonens and Popot, 2014 (J. Membrane Biol. 2014, 247(0): 759-796) and Zoonens et al., 2014 (I. Mus-Veteau (ed.), *Membrane proteins Production for Structural Analysis*, ©Springer Science+ business Media New York 2014, "Chapter 7 Amphipols: A General Introduction and Some Protocols", page 173-203).

In a particular embodiment, the amphipols that can be used in the compositions according to the invention are selected from the amphiphilic polymers comprising a homopolymer or copolymer of maleic anhydride or of polyacrylate, on which at least one hydrophobic group and a hydrophilic group are grafted, and having an average molecular weight comprised between 1,000 and 100,000 g/mol, preferably between 4,000 and 70,000 g/mol.

The first amphipols described in the state of the art are polyacrylate polymers in which certain carboxylate functions are functionalized with octylamine, or isopropylamine.

In a particular embodiment, the amphipols that can be used in the compositions according to the invention are the amphiphilic polymers as described in application WO 98/27434, and in particular the amphipol of the following formula (I):

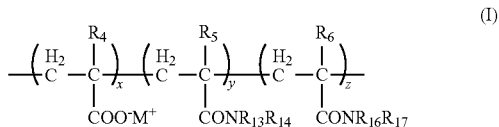

(I)

in which
- $R_4$, $R_5$, $R_6$, identical or different, are the hydrogen atom or the methyl radical,
- $R_{13}$, $R_{14}$, identical or different, are a linear or branched alkyl or alkenyl radical with 6 to 12 carbon atoms, and in addition one of the two can correspond to the hydrogen atom,
- $R_{16}$, $R_{17}$ are a ($C_1$ to $C_5$) alkyl radical, and in addition one of the two can correspond to the hydrogen atom,
- x, y, z correspond to the respective percentages of the units:
  - x being comprised between 20 and 90%
  - y being comprised between 10 and 80%
  - z being comprised between 0 and 60%, the average molecular weight being comprised between 500 and 100,000 g/mol, advantageously less than or equal to 50,000 g/mol, preferably between 1,000 and 50,000 g/mol.

All the molecular weights are given by weight.

Among the $R_{13}$ to $R_{14}$ alkyl radicals, there may be mentioned in particular the n-hexyl, n-heptyl, n-octyl, n-nonyl, n-decyl, n-undecyl, n-dodecyl radicals, the $C_6$-$C_{12}$ radicals having a secondary carbon or a tertiary carbon.

Among the $R_{13}$ to $R_{14}$ alkenyl radicals, there may be mentioned in particular the $C_6$-$C_{12}$ linear radicals mentioned above having one or two double bonds, or the same radicals having a secondary carbon or a tertiary carbon.

Among the $R_{16}$ to $R_{17}$ alkyl radicals, there may be mentioned in particular ethyl, isopropyl, n-propyl, n-butyl, isobutyl, sec-butyl, t-butyl, n-pentyl, sec-pentyl, t-pentyl, isopentyl.

The acrylic polymers with amphiphilic character of formula (I) are obtained in a known manner starting from acrylic polymer precursors, optionally commercially available or synthesizable by polymerization of monomers of acrylic acid or of methacrylic acid or of a mixture of these monomers.

In the latter case, copolymers are obtained, which by extension are included in the generic term "polymer".

The acrylic polymers with amphiphilic character of formula (I) result from the reaction of $R_{13}R_{14}NH$ and optionally $R_{16}R_{17}NH$ compounds with an acrylic polymer, which leads to a random distribution of the amides all along the chain. The polymer is converted to the salified form beforehand, or in a subsequent step. Such a synthesis method is described for example in March, J. ((1985) Advanced Organic Chemistry: Reactions, Mechanisms and Structure, pp. 372-374 (Wiley, New York)); Wang, T.K., Iliopoulos, I. & Audebert, R. ((1988) Polym. Bull 20, 577-582), and also described in application WO 98/27434, the contents of which are incorporated by reference.

Embodiment variants of the amphipols of formula (I) above are indicated hereunder:

According to a first variant, $R_{13}$, $R_{14}$ correspond to a hydrogen atom or to a linear alkyl radical with 6 to 12 carbon atoms, where $R_{13}$, $R_{14}$ cannot be the hydrogen atom simultaneously, preferably $R_{13}$ or $R_{14}$ is an n-octyl radical, the other $R_{14}$ or $R_{13}$ radical being a hydrogen atom.

According to a second variant, $R_{16}$, $R_{17}$ correspond to an alkyl radical selected from a group constituted by the isopropyl or isobutyl radicals or to a hydrogen atom, and $R_{16}$, $R_{17}$ cannot simultaneously correspond to the hydrogen atom.

According to a third variant
x is comprised between 30 and 80%
y is comprised between 20 and 70%
z is comprised between 0 and 50%, According to a fourth variant, the acrylic polymer with amphiphilic character is selected from the group constituted by the polymers in which
M+ is Na+ or K+
$R_{13}$ is an n-octyl, $R_{14}$ is H
x is comprised between 70 and 80%
y is comprised between 20 and 30%
z is 0%
The average molecular weight is comprised between 2,000 and 50,000 g/mol.

According to a fifth variant, the acrylic polymer with amphiphilic character is selected from the group constituted by the polymers in which M+ is Na+ or K+
$R_{13}$ is an n-octyl, $R_{14}$ is H
$R_{16}$ is an isopropyl, $R_{17}$ is H
x is comprised between 30 and 40%
y is comprised between 20 and 30%
z is comprised between 30 and 50%
The average molecular weight is between 2,000 and 50,000 g/mol.

In a particular embodiment, the amphipol is the polymer A8-35 of the following formula (Ia):

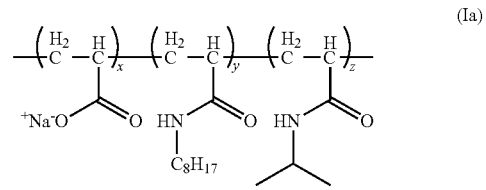

(Ia)

x, y, z correspond to the respective percentages of the units,
  x being comprised between 34 and 36%, preferably approximately 35%,
  y being comprised between 24 and 26%, preferably approximately 25%,
  z being comprised between 38 and 42%, preferably approximately 40%,
the average molecular weight being between 4,000 and 4,600 g/mol, preferably approximately 4,300 g/mol.

In another specific embodiment, the amphipol that can be used in the compositions according to the invention is selected from the poly(maleic anhydride)s, on which at least one hydrophobic alkyl chain and at least one hydrophilic group are grafted.

Preferably, it is a polymer of the following formula (II)

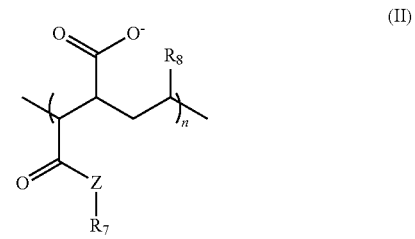

(II)

in which Z is a divalent radical, preferably O, S or NH, $R_7$ is a hydrophilic group, preferably an alkylated ammonium, and $R_8$ is a hydrophobic group, for example a linear carbon chain.

In a particular embodiment, the hydrophilic group $R_7$ is selected from the functional groups such as amines, alcohols or ketones.

The average molecular weight of these poly(maleic anhydride)s is preferably comprised between 1,000 and 70,000 g/mol, more preferably between 10,000 and 20,000 g/mol.

In another specific embodiment, the hydrophilic group is a carboxylate group or a positively charged group, preferably an ammonium, for example an alkylated ammonium of the following formula: $-(CH_2)_n-NH(CH_3)_2$ with n being comprised between 2 and 6, for example 3-(dimethylamino)-1-propylamine.

The alkylated ammonium is preferably attached to the maleic anhydride by an amide, ester or thioester function, preferably an amide function.

The hydrophobic alkyl chain is preferably selected from the linear alkyl chains of formula —$(CH_2)_n$— with n greater than or equal to 4, preferably greater than or equal to 6, preferably greater than or equal to 8, and for example comprised between 4 and 16, preferably between 8 and 12.

These polymers of maleic anhydrides can be selected in particular from the poly(maleic anhydride-alt-1-octadecene)s, the poly(maleic anhydride-alt-1-tetradecene)s and the poly(maleic anhydride-alt-1-decene)s, substituted with a hydrophilic group, preferably a positively charged group as defined above, and in particular an alkylated ammonium, such as 3-(dimethylamino)-1-propylamine.

In a specific embodiment, the amphipol used according to the invention is the substituted poly(maleic anhydride-alt-1-tetradecene) of the following formula (IIa):

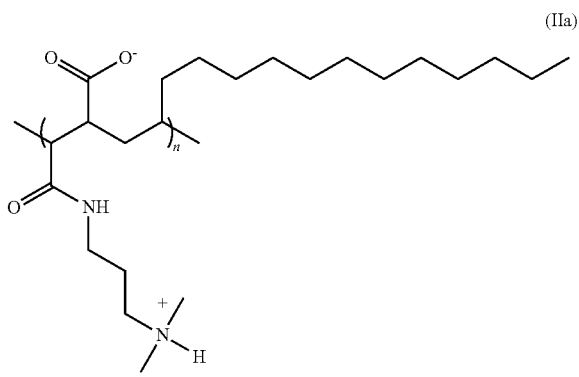

(IIa)

with an average molecular weight comprised between 10,000 and 14,000 g/mol, for example approximately 12,000 g/mol.

In another specific embodiment, the amphipol used according to the invention is the substituted poly(maleic anhydride-alt-1-decene) of the following formula (IIb):

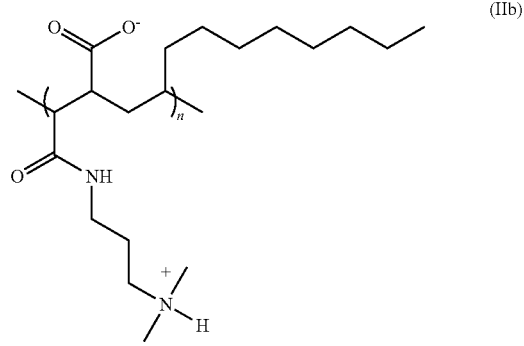

(IIb)

with an average molecular weight between 16,000 and 20,000 g/mol, for example approximately 18,500 g/mol.

In another specific embodiment, the amphipol used according to the invention is the substituted poly(anhydride-alt-1-octadecene) of the following formula (IIc):

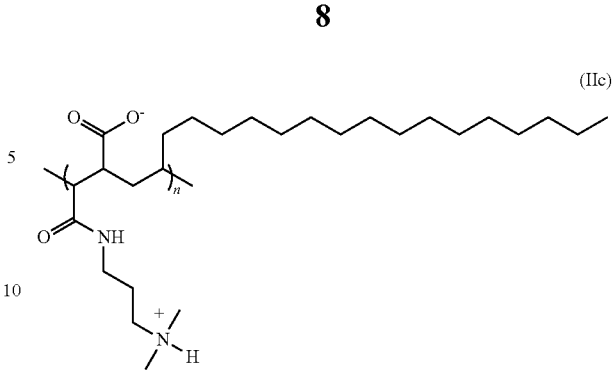

(IIc)

with an average molecular weight between 39,000 and 65,000 g/mol.

In a preferred embodiment, the amphipol is selected from PMAL C12 (CAS No.: [869857-14-7]), PMAL C8 (CAS No.: [869856-84-8]) and PMAL C16 (CAS No.: [869857-16-9]).

Some of these amphipol polymers and in particular the PMAL series (for example PMAL C12, PMAL C8 and PMAL C16) are manufactured and marketed by the company Anatrace.

The Amphoteric Polymers

The compositions according to the invention comprise an amphipol as described above, in combination with an amphoteric copolymer based on (meth)acrylate monomers, a part comprising a group of the following formula (III):

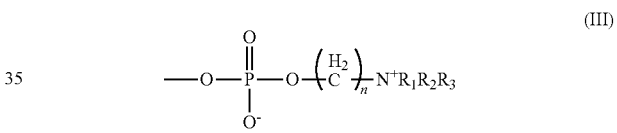

(III)

in which n is an integer from 1 to 6 (preferably 2),
$R_1$, $R_2$, $R_3$, identical or different, represent independently hydrogen or an alkyl with 1 to 6 carbons, substituted or not, preferably $R_1$, $R_2$ and $R_3$ are methyls.

For example, $R_1$, $R_2$, and $R_3$ according to formula (IV) can be methyl, ethyl, propyl, butyl, isobutyl, pentyl, hexyl. The number of alkyl substituents is from 1 to 3 and the substituents comprise hydroxy or aryl. Aryl includes benzyl or naphthyl.

The average molecular weight of the amphoteric copolymers that can be used according to the invention is preferably comprised between 100 and 1,000,000 g/mol, for example between 1,000 and 500,000 g/mol.

Furthermore, the amphoteric copolymers include a polymer prepared by polymerization of a monomer comprising a group of formula (III) with another polymerizable monomer.

In a specific embodiment, the monomer comprising a group of formula (III) is a monomer comprising phosphorylcholine and a vinyl group, in particular 2-acryloyloxyethyl phosphorylcholine, 2-methacryloyloxyethyl phosphorylcholine (referred to hereinafter by the abbreviation MPC), 2-(meth)acryloyloxyethoxyethyl phosphorylcholine, 6-meth(acryloyloxyhexyl phosphorylcholine), 10-(meth)acryloyloxyethoxynonyl phosphorylcholine, allyl phosphorylcholine, butenyl phosphorylcholine, hexenyl phosphorylcholine, octenyl phosphorylcholine, decenyl phosphorylcholine. These monomers can be prepared by known methods, described in particular in Japanese patent application No. 6325/79, and No. 154591/83.

The other polymerizable monomer comprises (meth)acrylate such as methyl (meth)acrylate, ethyl (meth)acrylate, n-butyl (meth)acrylate, isobutyl (meth)acrylate, pentyl (meth)acrylate, hexyl (meth)acrylate, heptyl (meth)acrylate, octyl (meth)acrylate, tridecyl (meth)acrylate, 2-hydroxyethyl methacrylate; a styrene monomer such as styrene, alpha-methylstyrene, styrene having a phenyl group substituted with one (or more) methyl group(s) and a styrene having a phenyl group substituted with chlorine; preferably it is functionalized methacrylate.

These polymers and their syntheses are also described in patent application EP 1 314 982 A1.

In particular, in a specific embodiment, amphoteric polymers based on (meth)acrylate monomers will be used, a part of these monomers comprising a phosphorylcholine group.

The percentage of monomers comprising the phosphorylcholine group is preferably between 1 and 100%, for example comprised between 1 and 50% or between 5 and 10%.

Preferably, it is an amphoteric copolymer based on 2-methacryloyloxyethyl phosphorylcholine (MPC), in particular a methacrylate monomer comprising a phosphorylcholine group and another methacrylate monomer comprising a hydrophobic group, an anionic group, a cationic group and/or a group allowing formation of hydrogen bonds.

A hydrophobic group is selected from
linear or branched $C_4$ to $C_{30}$ alkyls;
linear or branched $C_4$ to $C_{30}$ alkyls comprising at least one cycloalkyl;
$C_4$ to $C_{30}$ hydrocarbon-containing chains comprising at least one double bond;
$C_4$ to $C_{30}$ hydrocarbon-containing chains comprising at least one triple bond; or,
$C_4$ to $C_{30}$ hydrocarbon-containing chains comprising at least one aromatic ring.

Preferably, the hydrophobic group is selected from the linear alkyl chains of formula —$(CH_2)_n$— with n greater than or equal to 4, preferably greater than or equal to 6, preferably greater than or equal to 8, and for example comprised between 4 and 16, preferably between 8 and 12.

An anionic group can be selected in particular from those comprising a carboxylate radical and in particular the ($C_1$-$C_5$) alkyl carboxylates, those comprising a sulphonate radical, and in particular the ($C_1$-$C_5$) alkyl sulphonates and those comprising a phosphonate radical, and in particular the ($C_1$-$C_5$) alkyl phosphonates.

A cationic group can be selected in particular from a $(CH_2)_n$—$NR_9R_{10}R_{11}$ radical, n being an integer from 1 to 5 and $R_9$, $R_{10}$ and $R_{11}$, identical or different, being hydrogen or a ($C_1$-$C_4$) alkyl chain.

The compounds allowing formation of hydrogen bonds are well known to a person skilled in the art. An example of a group allowing formation of hydrogen bonds comprises the amines, alcohols, thiols, aldehydes, acids or ketones.

Preferred copolymers of MPC are marketed in particular by the company NOF Corporation under the trade name Lipidure® or Biolipidure® and, in particular, have the following general formula (IV):

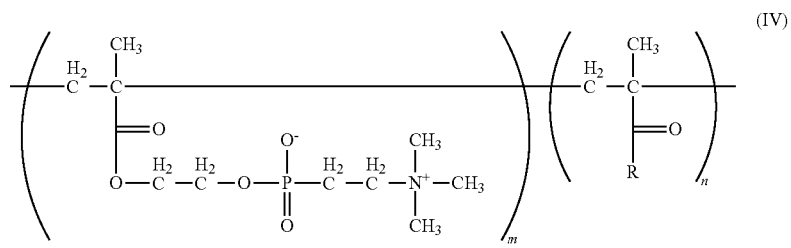

in which R is a hydrophobic group as defined above, with m and n corresponding to the respective percentages of the two monomers and m is comprised between 1 and 99%, for example between 1 and 50% or between 1 and 10%, and n is comprised between 1 and 99%, for example between 50 and 99% or between 90 and 99%.

According to a more specific embodiment, the amphoteric polymer of 2-methacryloyloxyethyl phosphorylcholine (MPC) is an amphoteric copolymer of MPC and of functionalized methacrylate with a linear alkyl chain of formula (—$CH_2$)$_n$— with n greater than or equal to 4, or greater than or equal to 6, or greater than or equal to 8, and for example comprised between 4 and 16, for example between 8 and 12.

By way of preferred example, Biolipidure™ 206, Biolipidure™ 203, Biolipidure™ 802 or also Biolipidure™ 1201, marketed by the company NOF Corporation, will be selected for preparing the immunoassay compositions according to the invention.

Use of the Compositions According to the Invention

The immunoassay compositions according to the invention described above are advantageously used as stabilizers and/or blocking agents.

Within the meaning of the invention, by "stabilizer" is meant a compound or composition capable of promoting stability (thermal and over time) of the binding partner (which may be denatured after storage at ambient temperature, for example), of reducing its degradation by hydrolysis, of preventing its aggregation and/or more generally of contributing to maintenance of the native conformation of the binding partner and of its capacity for binding the analyte to be detected. The thermal stability of an immunoassay reagent can be determined by comparing the detection signal before storage thereof at ambient temperature and after storage at ambient temperature for 30 days. A reagent is stable if the signal measured at 30 days is within values close to those of the signal measured at t0, for example comprised between 90% and 110% of the signal measured at t0.

By "blocking agent" is meant a compound or composition that is able to reduce the non-specific interactions between a binding partner and a non-specific molecule of an immunoassay, and therefore reduce the signal obtained in the presence of a negative control ("background noise").

In particular, the compositions according to the invention are useful for reducing the non-specific interaction between at least one immunoassay reagent, preferably a binding partner, labelled or not, and a solid phase.

In another embodiment, the aqueous compositions according to the invention are useful for reducing the non-specific interaction between
(i) an immunoassay positive control and/or an immunoassay standard and/or an immunoassay adjuster, and
(ii) a solid phase.

The term "non-specific interaction" is understood as opposed to the specific interaction of the binding partner with the analyte.

By specific interaction is meant a binding preference (affinity) of a binding partner for the target analyte at least 2 times, preferably at least 5 times, and more preferably at least 10 or 20 times greater than that measured for a non-specific molecule (for example one or more arbitrary molecules that do not a priori contain the recognition sites specific to the binding partner).

Here, the term "analyte" denotes a substance contained in a sample, which must be detected, identified and/or quantified by an analysis. It must therefore be understood in the broad sense as denoting a chemical, biological or biochemical substance. By way of examples of analytes, a protein, a peptide, a hapten, a polysaccharide or an oligosaccharide may be mentioned.

The term "solid phase" within the meaning of the invention refers to any insoluble material. The solid phase in an immunoassay is preferably selected for attracting and immobilizing a capture reagent. In another alternative, the solid phase comprises a charged substance, having a charge opposite to the capture reagent, or to a substance conjugated with the capture reagent. The solid phase can be for example plastic, a magnetic or non-magnetic metal, glass or silicone, and in particular a test tube, a microplate, beads, microparticles, a chip, a cone or any other configuration known to a person skilled in the art for carrying out an immunoassay.

Aqueous Solutions Comprising the Compositions According to the Invention and an Immunoassay Reagent The aqueous solutions are obtained by diluting an immunoassay reagent in a solvent comprising water and the compositions according to the invention containing the amphipol and amphoteric polymers as described in the preceding sections.

Thus, another aspect of the invention relates to an aqueous solution comprising the composition according to the invention as defined above and at least one immunoassay reagent.

Within the meaning of the invention, the term "immunoassay reagent" refers to any reagent intended to interact specifically with an analyte or a binding partner.

Of course, the prefix "immuno" in the term "immunoassay", for example, is not to be considered in the present application as indicating strictly that said binding partner is necessarily a partner of immunologic origin, such as an antibody or an antibody fragment.

In fact, as is well known to a person skilled in the art, this term is used more broadly for also denoting tests and methods in which the binding partner is not a partner of immunologic origin or nature, but consists for example of a receptor of the analyte that it is desired to detect and/or quantify. A condition is that the binding partner in question should be capable of binding specifically to the analyte sought. Thus, the term ELISA is commonly used for assays that use binding partners that are not immunologic in the strict sense, covered more generally by the English term "ligand binding assay", whereas the term "immuno" is included in the full title corresponding to the acronym ELISA. For the sake of clarity and uniformity, the term "immuno" is used in the present application to denote any biological analysis using at least one binding partner that is able to bind to the analyte sought and to detect and/or quantify the latter, preferably specifically, even when said binding partner is not of an immunologic nature or origin in the strict sense.

By way of example of reagents of the binding partner type present in the aqueous solutions according to the invention, there may be mentioned antibodies, antibody fragments, Nanofitins, receptors, aptamers, DARPins or any other macromolecule selected specifically so as to obtain a specific interaction with the analyte, and preferably an interaction of high affinity with the analyte, with a $K_D$ as measured by surface plasmon resonance less than 1 µM, in particular less than 100 nM and preferably less than 10 nM.

The polyclonal antibodies can be obtained by immunization of an animal with an immunogen, followed by recovery of the required antibodies in purified form, by taking the serum of said animal, and separating said antibodies from the other constituents of the serum, for example by affinity chromatography on a column on which an antigen is fixed that is recognized specifically by the antibodies, in particular the immunogen, or using a protein A or G.

The monoclonal antibodies can be obtained by the hybridoma technique that is well known to a person skilled in the art. The monoclonal antibodies can also be recombinant antibodies obtained by genetic engineering, by techniques that are well known to a person skilled in the art.

As examples of antibody fragments, the fragments Fab, Fab', F(ab')2 as well as scFv (single chain variable fragment), dsFv (double-stranded variable fragment) may be mentioned. These functional fragments can in particular be obtained by genetic engineering.

The Nanofitins (trade name) are small proteins which, like antibodies, are capable of binding to a biological target, thus allowing it to be detected, captured or quite simply targeted within an organism.

The aptamers are oligonucleotides, generally RNA or DNA, identified in banks containing up to $10^{15}$ different sequences, by a combinatorial method of in vitro selection called SELEX for "Systematic Evolution of Ligands by Exponential Enrichment" (Ellington A D and Szostak J W, 1990, Nature, 346: 818-822). Most of the aptamers are RNA compounds, on account of the capacity of RNA to adopt varied and complex structures, which makes it possible to create cavities of varied geometries on its surface, allowing various ligands to be fixed. They are biochemical tools of interest that can be used in biotechnological, diagnostic or therapeutic applications. Their selectivity and their properties of fixation of ligands are comparable to those of antibodies.

The "DARPins", denoting Designed Ankyrin Repeat ProteINS (Boersma Y L and Plütckthun A, 2011, Curr. Opin. Biotechnol, 22: 849-857), are another class of proteins capable of mimicking antibodies and of binding with high affinity and selectivity to target proteins. They are derived from the family of ankyrin proteins, which are adaptor proteins that allow the integral membrane proteins to be fixed to the spectrin/actin network that constitutes the "backbone" of the cell plasma membrane. The structure of the ankyrins is based on repetition of a motif of approximately 33 amino acids, and the same applies to the DARPins. Each motif has a secondary structure of the helix-turn-helix type. The DARPins contain at least three, preferably four to five repeat motifs and are obtained by screening combinatorial banks.

In a particular embodiment, the immunoassay reagent comprised in the aqueous solutions according to the invention is selected from a binding partner intended to detect or quantify an analyte in a biological sample that may contain it, where said binding partner can be labelled (for example a labelled antibody) or not, a positive control, a standard or an adjuster of an immunoassay.

By "positive control" is meant a compound able to produce a signal complying with the signal expected by the immunoassay in the presence of a sample containing the analyte to be detected.

By "standard" is meant a compound used for producing a standard range, a necessary step that makes it possible to carry out quantification of an analyte. The relationship between the known concentrations or quantities of the standard and the signal obtained by immunoassay is expressed mathematically: this is the calibration curve.

By "adjuster" is meant a compound used for adjusting the measurement of the immunoassay of the analyte. In this case, the signal generated by the adjuster and its concentration is known. The adjuster serves for adjusting a calibration curve generated beforehand, taking into account the ageing of the immunoassay reagents or the conditions of application.

The binding partner present in the aqueous solutions according to the invention can be labelled, i.e. bound, preferably covalently, directly or indirectly to a label. Very often, labelling is carried out by chemical coupling using a cross-linker. It is then called a conjugated binding partner. An example of a labelled binding partner that is often used is an antibody conjugated to an enzyme, also called conjugated antibody.

By "label" is meant in particular any molecule capable of directly or indirectly generating a detectable signal. A non-limitative list of these detection labels consists of:
- enzymes that produce a signal detectable for example by colorimetry, fluorescence, luminescence, such as horseradish peroxidase, alkaline phosphatase, beta-galactosidase, glucose-6-phosphate dehydrogenase,
- chromophores such as fluorescent compounds, luminescent compounds, dyes,
- radioactive molecules such as $^{32}P$, $^{35}S$ or $^{125}I$,
- fluorescent molecules such as Alexa or phycocyanins, and
- electrochemiluminescent salts such as organometallic derivatives based on acridinium or ruthenium.

Thus, in a particular embodiment, the aqueous solution according to the invention comprises, besides the polymers described in the preceding sections, an antibody conjugated to a label, also called "detection antibody".

Indirect detection systems can also be used, such as for example ligands capable of reacting with an anti-ligand. The ligand then corresponds to the label, to constitute, with the binding partner, the conjugate.

Ligand/anti-ligand pairs are well known to a person skilled in the art, which is the case for example of the following pairs: biotin/streptavidin, hapten/antibody, antigen/antibody, peptide/antibody, sugar/lectin, polynucleotide/complementary polynucleotide.

The anti-ligand may then be detectable directly by the direct detection labels described or may itself be detectable by another ligand/anti-ligand pair, and so on.

The quantity of immunoassay reagents present in the aqueous solution according to the invention depends on the final use thereof. In a particular embodiment, the immunoassay reagent is a labelled antibody present at a rate from 100 pg/mL to 20 µg/mL, for example from 20 ng/mL to 3 µg/mL.

The polymer compositions according to the invention are advantageously used for replacing the molecules usually added with the reagents as stabilizer and/or blocking agent, in particular macromolecules of animal origin.

Consequently, in a particular embodiment, the aqueous solution according to the invention is characterized in that it does not comprise a stabilizer and/or blocking agent of animal origin selected from animal sera, hydrolyzed or non-hydrolyzed caseins, skimmed milk, in particular powdered skimmed milk, bovine or human albumin, and gelatins, also called generically "filler protein" even if macromolecules other than proteins are used.

The aqueous solution preferably comprises the amphipol and the amphoteric copolymer as described in the preceding paragraphs in effective concentrations for acting as a blocking agent in an immunoassay. These effective concentrations will be determined by a person skilled in the art, in particular as a function of the concentration of reagents used, the nature of the reagents, the stabilizing and/or blocking effect required and/or the type of immunoassay.

Typically, final concentrations of amphipols in the aqueous solution comprised between 0.01% and 0.2% (weight/volume), preferably between 0.02% and 0.05%, for example 0.02%, and final concentrations of amphoteric polymers in the aqueous solution comprised between 0.01% and 0.3% (weight/volume), preferably between 0.03% and 0.08%, for example 0.05%, will be used.

The aqueous solution can additionally contain other constituents, and in particular a buffer, a detergent, salts, a dye, an emollient, a preservative, etc.

Immunoassay Kit According to the Invention

The aqueous solutions of the invention are particularly useful for a method for detecting an analyte, in a biological sample that may contain it, comprising an immunoassay by contacting said sample with at least one binding partner to the analyte.

Thus, the immunoassay kits comprising the aqueous solutions according to the invention constitute another subject of the invention.

The immunoassay kits contain one or more compounds necessary for carrying out an immunoassay and in particular one or more binding partners to the analyte, labelled or not, and all the compounds necessary for detecting a specific interaction between the binding partner or partners to the analyte.

When it is an immunoassay of the sandwich type, the immunoassay kit then comprises two binding partners, one of the two binding partners being labelled, to form the "tracer" or "detection partner", and the other partner being captured on a solid phase, also called "capture partner".

These immunoassay kits according to the invention can further comprise one or more of the following elements:
- a solid phase, for example a microplate or cones, sensitized with capture partners, for example a capture antibody,
- a washing solution,
- a labelled binding partner, for example a conjugated antibody,
- a composition according to the invention without an immunoassay reagent,
- a composition according to the invention or aqueous solution according to the invention comprising a reagent as positive control,
- a composition according to the invention or aqueous solution according to the invention comprising one or more reagents of known concentration as a standard, a composition according to the invention or aqueous solution according to the invention comprising a reagent of known concentration as an adjuster, instructions for carrying out the immunoassay.

In a particular embodiment for an immunoassay carried out by an automated device, for example of the Vidas® type, the immunoassay kit according to the invention is a box comprising the following separate elements:

cones sensitized with binding partners, for example specific antibodies of the analyte to be detected, a cartridge, i.e. a solid phase comprising a plurality of wells, for example from 4 to 20, some of which are preferably sealed, at least one of the wells comprising an aqueous solution according to the invention, for example an aqueous solution containing a reagent, preferably a labelled antibody specific to the analyte to be detected, if applicable, a composition according to the invention without an immunoassay reagent, if applicable, a composition according to the invention or aqueous solution according to the invention comprising a reagent as a positive control, if applicable, a composition according to the invention or aqueous solution according to the invention comprising a reagent, of known concentration, as an adjuster.

The solid phase and the cartridge as such, as described in the above kits, also form part of the invention.

Method of Carrying Out an Immunoassay According to the Invention

The invention also relates to any immunoassay method for determining the presence or for quantification of an analyte, in a biological sample that may contain it, comprising the use of a composition or aqueous solution of the invention in particular as a blocking agent and/or stabilizer.

Thus, the invention further relates to a method for detecting an analyte in a biological sample that may contain it, comprising i. an immunoassay by contacting said sample with at least one binding partner to the analyte, ii. if applicable, a test for checking the validity of the immunoassay by contacting a positive control with said one or more binding partners to the analyte, iii. reading the immunoassay, iv. determining the presence of said analyte in the test sample when the signal obtained by the immunoassay in step i is greater than a threshold value of the immunoassay, said method comprising the use of a composition or aqueous solution according to the invention.

In an embodiment of the above detection method, the immunoassay carried out in step (i) uses a composition or aqueous solution according to the invention.

In another embodiment of the above detection method, the control test carried out in step (ii) is obtained using an aqueous solution according to the invention in which the reagent is a control.

Naturally, the two preceding embodiments can be combined.

The test sample in the context of the invention can be of various origins, for example of food, environmental, biological, veterinary, clinical, pharmaceutical or cosmetic origin.

Among the samples of food origin, a sample of milk products (yoghurts, cheeses, etc.), meat, fish, egg, fruit, vegetable, water, drinks (milk, fruit juice, fizzy drinks, etc.) may be mentioned non-limitatively. Of course, these samples of food origin can also be taken from sauces or more elaborate dishes or unprocessed or partially processed raw materials. A food sample can also be derived from animal feed, such as cakes or meal for animals. All these samples, if they are not liquid, are treated beforehand so that they are in liquid form.

As stated above, the sample can be of environmental origin and can consist, for example, of a sample taken from a surface, from water, etc.

The sample can also consist of a biological sample, of human or animal origin, which can correspond to samples of biological fluid (urine, whole blood or derivatives such as serum or plasma, saliva, pus, cerebrospinal fluid, etc.), stool (for example choleraic diarrhea), samples taken from the nose, throat, skin, wounds, organs, tissues or isolated cells, and swab samples. Obviously this is a non-limitative list.

In general, the term "sample" refers to a part or to a quantity, more particularly a small part or a small quantity, taken from one or more entities for the purposes of analysis. This sample can optionally have undergone a preliminary treatment, involving for example steps of mixing, diluting or also grinding, especially if the starting entity is in the solid state.

The sample analyzed is generally likely to contain, or suspected of containing, at least one analyte representative of the presence of microorganisms, of a disease, or of a physiological condition, to be detected, characterized or monitored.

The steps of this method for detecting an analyte by immunoassay are steps well known to a person skilled in the art that were described above. In particular, the first step consists of contacting the test sample with one or more binding partners to the analyte, preferably at least two binding partners for a sandwich assay. As described above, one of the two partners can be coupled to a label to form a conjugate or a tracer. The other binding partner can be captured on a solid support, as known to a person skilled in the art.

The measured signal emitted by the conjugate is then proportional to the quantity of analyte in the biological sample.

The immunoassay i) and the control test ii) can be carried out in any order, simultaneously or successively, on the same solid support or not.

Reading of the immunoassay is also a step well known to a person skilled in the art, which depends on the assay used.

Finally, the last step consists of determining the presence of said analyte in the test sample when the signal obtained by the immunoassay in step i) is greater than the detection threshold of the immunoassay. This step is also well known to a person skilled in the art.

A further subject of the invention relates to a method for quantifying a target analyte by immunoassay in a biological sample that may contain said analyte, comprising i. an immunoassay by contacting said sample with at least one binding partner to the analyte, ii. if applicable, a test for checking the validity of the immunoassay by contacting a positive control with said one or more binding partners to the analyte, iii. reading the immunoassay if the test for checking validity is positive, and iv. determining the quantity of said analyte in the test sample by comparing the signal from the immunoassay with a standard curve, in which the reagent is an immunoassay adjuster, said method comprising the use of a composition or aqueous solution according to the invention.

In an embodiment of the above detection method, the immunoassay carried out in step (i) uses a composition or aqueous solution according to the invention.

In another embodiment of the above quantification method, the control test carried out in step (ii) is obtained using an aqueous solution according to the invention in which the reagent is a control.

In yet another embodiment of the above quantification method, the standard curve used in step (iv) is obtained using an aqueous solution according to the invention in which the reagent is an immunoassay adjuster.

Naturally, the preceding three embodiments can be combined.

Of course, the description of the samples and of the various process steps described in the context of the method for detecting a target analyte applies to the method for quantifying a target analyte. The only difference consists of the last step, which consists of determining the quantity of analyte by comparing with a standard curve, as explained above.

In a specific embodiment of the methods described above, the method by immunoassay according to the invention comprises contacting said sample with at least two binding partners to said analyte, P1 and P2, sequentially or simultaneously, one of the two partners P2 being labelled to show the presence of said analyte, if it is present, the other partner P1 preferably being immobilized on a solid phase, said labelled partner P2 being contained in at least one composition according to the invention or at least one aqueous solution according to the invention, as described above, to form, if applicable, a P1/analyte/P2 complex, detection of the presence of said complex formed allowing conclusions to be drawn concerning the presence or the quantity of analyte in the sample.

In another embodiment, the method by immunoassay comprises contacting said sample with at least one binding partner P1 to said analyte and a reagent R1 that competes with the analyte, said binding partner P1 preferably being immobilized on a solid phase, said reagent R1 being labelled to show indirectly the presence of said analyte, and said reagent R1 being contained in at least one composition according to the invention or at least one aqueous solution according to the invention, to form a P1/R1 complex, detection of the presence of said complex formed allowing conclusions to be drawn indirectly concerning the absence or the quantity of analyte in the sample.

The same features and preferences described in the preceding sections, in particular regarding the choice of the particular polymers and compounds in the different steps of the immunoassay, also apply to the methods of detection and quantification according to the invention.

The methods of immunoassay of the invention comprise in particular the use of the immunoassay kits of the invention described above.

The invention will be better understood from the following examples, which are given for purposes of illustration and are non-limitative.

EXAMPLES

Comparison of Different Formulations of Diluent for Reagents According to the Invention, for Assay of Cardiac Troponin I Investigation of diluents for conjugated antibodies for immunoassay of cardiac Troponin I was carried out with the VIDAS® automated immunoanalyzer (bioMérieux). The disposable cone serves both as the solid phase for the reaction and as a pipetting system. The cartridge of the automated analyzer is made up of 10 wells (X0 to X9) covered with sealed and labelled aluminium foil. The first well (X0) comprises a precut part to facilitate introduction of the sample. The last well (X9) is an optical cuvette in which the fluorescence of the substrate is measured. The various reagents necessary for the analysis are contained in the intermediate wells. All the steps of the assay are thus carried out automatically by the instrument. They are constituted by a succession of cycles of aspiration and return of the reaction mixture. The immunoassay of cardiac Troponin I was carried out by a single-step sandwich assay.

a) Sensitization and Passivation of the Cones

The characteristics and the suppliers of the antibodies used are presented in Table 1 below. The cones were sensitized with 300 µL of a solution of the monoclonal antibodies 19C7 and B90 each diluted to 2.5 µg/mL in PBS buffer pH 6.2. After incubation for approximately 20 h at +18/25° C. with the sensitizing solution, the cones were emptied. Then 300 µL of this same solution containing 10 g/L of bovine albumin is added. Passivation continues at +18/25° C. overnight. The cones are emptied, dried, and then stored, protected against moisture, at +4° C. until used.

TABLE 1

Antibodies used for immunoassay of cardiac Troponin I

| Name of the antibody | Target | Supplier (Cat. No.) |
|---|---|---|
| 19C7 | TnI | Hytest (4T21-19C7) |
| B90 | TnI | SDIX (B9085MA06-MA) |
| 3D5F7 | TnI | bioMerieux (non-commercial) |
| 7B9 | TnC | Hytest (4T27-7B9) |

The abbreviation TnI corresponds to cardiac Troponin I and the abbreviation TnC corresponds to cardiac Troponin C. The abbreviation Cat. No. corresponds to the supplier's catalogue reference.

b) Preparation of Diluents for Conjugated Antibodies and Solutions of Conjugates Various diluent solutions for conjugated antibodies were prepared according to Table 2.

TABLE 2

Composition of the various diluents for conjugated antibodies.

| Compound | REF diluent | Diluent 1 | Diluent 2 | Diluent 3 Diluent of the invention |
|---|---|---|---|---|
| PBS pH 6.4 | X | X | X | X |
| Horse serum 5% | X | X | | |
| Biolipidure 206[1] 0.05% | | | X | X |
| PMAL C12[2] 0.02% | | X | | X |

X indicates that the compound is present in the diluent.
[1]Marketed by the company NOF Corporation ref. Biolipidure-206.
[2]CAS No. 869857-14-7 marketed by the company Anatrace ref. P5012.

The diluents REF and 1 to 3 were used for preparing various solutions of conjugates. Each solution of conjugate contains the 2 monoclonal detection antibodies, 3D5F7 and 7B9 (described in Table 1), in the form of Fab' fragments coupled to alkaline phosphatase. These conjugated antibodies were diluted to approximately 0.5 µg/mL each in the various diluents described in Table 2 above.

c) Immunoassay Procedure

The solutions of conjugates were tested with natural samples (points A, B, C, E and G, for which the concentrations of Troponin I are known) or a PBS-BSA buffer as a blank sample (point O).

Once the VIDAS® cone is in contact with the sample, the immunologic reaction begins, as the capture antibodies are immobilized on said cone. The automated analyzer mixes the test sample (135 µL) with 270 µL of the solution of conjugate.

Incubation takes approximately 9 minutes at 37° C. and allows specific binding of cardiac Troponin I to the antibodies adsorbed on the cone on the one hand and to the conjugated antibodies (detection antibodies) on the other hand. Then the unbound components are removed by washing 3 times with buffer Tris 200 mM pH 7.8, NaCl 300 mM, Triton X-100 0.2%. In the final detection step, the substrate 4-methylombelliferyl phosphate is aspirated and then returned to the cone; the enzyme of the conjugated antibodies catalyzes the reaction of hydrolysis of this substrate to 4-methylombelliferone, the emitted fluorescence of which is measured at 450 nm. The value of the fluorescence signal (RFV=relative fluorescence value) is proportional to the concentration of the antigen present in the sample.

d) Results

Table 3 presents the fluorescence signals (RFV=relative fluorescence value) determined by the VIDAS® automated analyzer when the signals obtained are compared with the conjugated antibodies diluted in the reference diluent (REF) (prior art), and the various formulations of diluents (Table 2).

TABLE 3

Results obtained with the various diluent formulations

| Item | REF diluent | Diluent 1 | Diluent 2 | Diluent 3 Diluent of the invention |
|---|---|---|---|---|
| RFV signal point O (blank) | 7.5 | 9.8 | 7.0 | 4.5 |
| RFV signal point A (4.0 ng/L) | 13 | 13 | 18 | 18 |
| RFV A/RFV O | 1.7 | 1.3 | 2.6 | 4.0 |
| RFV A – RFV O | 5.5 | 3.3 | 11.0 | 13.5 |
| RFV signal point B (10.2 ng/L) | 26.0 | 25.0 | 31.5 | 33.5 |
| RFV B/RFV O | 3.5 | 2.6 | 4.5 | 7.4 |
| RFV B – RFV O | 18.5 | 15.3 | 24.5 | 29.0 |

As can be seen in Table 3, adding PMAL C12 to REF diluent (Diluent 1) has almost no effect on the signals observed. However, replacing horse serum with Biolipidure 206 (Diluent 2) improves the dynamics at the bottom of the range (higher signals of points A and B), but does not allow the background noise to be reduced (signals of points O around 7 RFV). It is addition of PMAL C12 to this diluent (Diluent 3, diluent of the invention) that gives a significant reduction in background noise, which changes from 7 to 4.5 RFV. The result is a significant increase in the ratios RFV A/RFV O and RFV B/RFV O. Thus, the combination of Biolipidure 206 and PMAL C12 has an unexpected synergistic effect.

d) Stability of the Conjugated Antibodies Diluted in the Various Diluent Formulations The conjugated antibodies (detection antibodies) are diluted to 0.5 µg/mL in the various diluent formulations presented in Table 2 and are used immediately for assaying the samples (A, B, C, E and G). The results obtained correspond to the results at time T0. The detection antibodies diluted in the various diluents are then stored for 1 month, either at +2/8° C. (normal condition), or at +18/25° C. (accelerated stability condition). After one month, the same samples are re-assayed on VIDAS under the same conditions with the diluted solutions of detection antibodies stored for 1 month. For each condition, the ratio of the RFV signal obtained at the end of one month to the RFV signal obtained at T0 is calculated. The results are presented in Table 4.

TABLE 4

Stability of the conjugated antibodies in the various diluent formulations

| Point (Troponin conc.) | RFV signal 1 month/RFV signal T0 | | | | | | | |
|---|---|---|---|---|---|---|---|---|
| | REF diluent | | Diluent 1 | | Diluent 2 | | Diluent 3 | |
| | 2/8° C. | 18/25° C. | 2/8° C. | 18/25° C. | 2/8° C. | 18/25° C. | 2/8° C. | 18/25° C. |
| Point A (4.0 ng/L) | 1.08 | 1.12 | 1.15 | 0.96 | 1.14 | 0.97 | 1.06 | 1.03 |
| Point B (10.2 ng/L) | 1.10 | 1.08 | 1.06 | 0.96 | 0.97 | 0.89 | 0.99 | 0.91 |
| Point C (18.3 ng/L) | 0.98 | 1.00 | 1.04 | 0.98 | 0.94 | 0.81 | 1.00 | 0.89 |
| Point E (93.6 ng/L) | 0.97 | 1.12 | 1.01 | 0.98 | 0.98 | 0.86 | 1.00 | 0.92 |
| Point G (590 ng/L) | 1.01 | 0.93 | 1.03 | 0.99 | 1.02 | 0.87 | 1.02 | 0.93 |

The ratios >=1.10 or =<0.90 are highlighted in grey.

For a formulation of conjugated antibody to be regarded as stable, the signal ratios must mainly be included within the range [0.90-1.10]. Diluent 2, which contains Biolipidure 206, does not make it possible to obtain acceptable stability values in the absence of horse serum (comparative stabilizer present in the REF diluent). However, by adding PMAL C12 to Biolipidure 206, satisfactory values can be obtained for the various concentrations tested (see Diluent 3).

e) Effect of the Polymer PMAL C8

Diluent 4 has the same composition as Diluent 3 (Table 2), except that PMAL C12 in Diluent 3 is replaced with PMAL C8 in Diluent 4. The two diluents were compared using a new panel of samples containing known concentrations of Troponin I. These samples were tested by immunoassay on VIDAS according to the procedure described in c) with the following modification. The conjugated antibodies were each diluted to a concentration of 0.9 µg/mL, either in Diluent 3, or in Diluent 4. The results obtained (RFV signals) are presented in Table 5.

TABLE 5

Comparison of the diluents of the invention containing PMAL C12 or PMAL C8

| Troponin I conc. (ng/L) | Solution of conjugate with Diluent 3 (PMAL C12 at 0.02%) | Solution of conjugate with Diluent 4 (PMAL C8 at 0.02%) |
| --- | --- | --- |
| 0.001 | 8 | 8 |
| 2.83 | 20 | 17 |
| 10.0 | 45 | 42 |
| 21.8 | 77 | 71 |
| 49.7 | 163 | 152 |

Diluent 3 containing PMAL C12 and Diluent 4 containing PMAL C8 give equivalent RFV signals. PMAL C8 therefore has the same unexpected synergistic effect as PMAL C12.

f) Synergistic Effect of PMAL C12 and Biolipidure 206 for Non-Compliant Batches of Conjugated Antibodies Depending on the purification conditions, storage conditions or for any other reason, certain batches of conjugated antibodies may have increased background noise, of the order of 15-20 RFV instead of the 4-8 RFV usually observed. Quality control carried out prior to batch release makes it possible to reject these non-compliant batches of conjugated antibodies, which will not be used in the end product (the immunoassay kit).

TABLE 7

Effect of the concentrations of PMAL C12 and Biolipidure 206 in Diluent 3 on the signal/noise ratios of the non-compliant batches of conjugated antibodies

| | Concentration of PMAL C12 + Biolipidure 206 | | |
| --- | --- | --- | --- |
| Item | 0.02% + 0.05% (Diluent 3) | 0.02% + 0.1% | 0.05% + 0.1% |
| RFV signal point O (blank) | 16.0 | 12.0 | 8.9 |
| RFV signal point A (4.0 ng/L) | 32 | 31 | 30 |
| RFV A/RFV O | 2.0 | 2.6 | 3.4 |
| RFV A − RFV O | 16.0 | 19.0 | 21.1 |
| RFV signal point B (10.2 ng/L) | 43.7 | 31.0 | 30.0 |
| RFV B/RFV O | 2.7 | 3.8 | 4.9 |
| RFV B − RFV O | 27.7 | 33.5 | 34.6 |

On using Diluent 3, which contains 0.02% of PMALC12 and 0.05% of Biolipidure 206, background noise of 16 RFV is observed with two non-compliant batches of conjugated antibodies. By increasing the concentration of PMALC12 to 0.05% and that of Biolipidure 206 to 0.1%, it is possible to reduce this background noise to 8.9 RFV, which allows a considerable improvement in the signal/noise ratio and makes it possible to envisage the use of such batches in an immunoassay. The higher initial background noise of these non-compliant batches requires higher concentrations of PMAL C12 and of Biolipidure 206 in order to demonstrate their synergistic blocking effect.

The invention claimed is:

1. A composition for immunoassay, comprising:
   (i) an amphipol selected from the group consisting of:
      (ia) a substituted poly(maleic anhydride-alt-1-tetradecene) of the following formula (IIa):

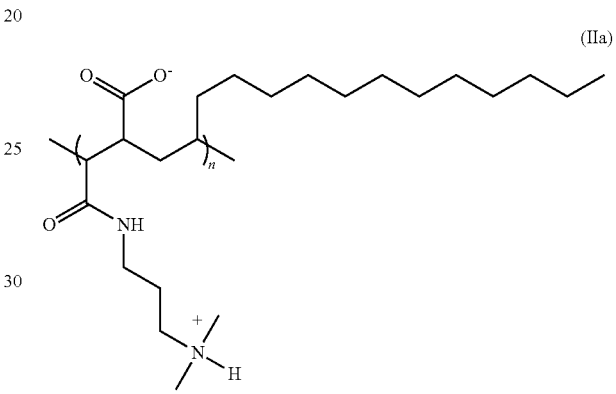

with an average molecular weight between 10,000 and 14,000 g/mol, and
      (ib) a substituted poly(maleic anhydride-alt-1-decene) of the following formula (IIb):

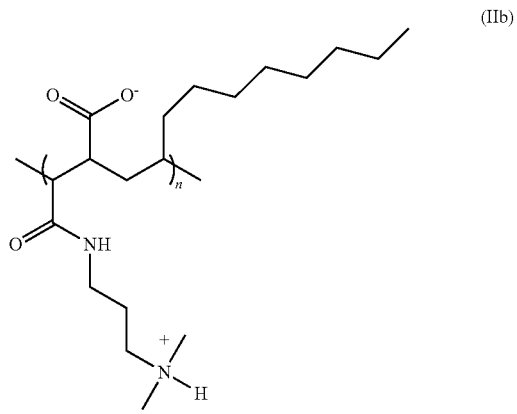

with an average molecular weight between 16,000 and 20,000 g/mol; and
   (ii) an amphoteric copolymer based on a monomer of 2-methacryloyloxyethyl phosphorylcholine (MPC) and another methacrylate monomer functionalized with an anionic group.

2. The composition according to claim 1 wherein:
   the amphipol is present in the composition at a concentration of between 0.02% and 0.05%, and the amphoteric copolymer is present in the composition at a concentration of between 0.05% and 0.1%.

3. An aqueous solution comprising the composition according to claim 1 and at least one immunoassay reagent.

4. The aqueous solution according to claim 3, wherein the immunoassay reagent is a binding partner intended to detect or quantify an analyte in a biological sample that may contain the analyte.

5. The aqueous solution according to claim 3, wherein the aqueous solution does not comprise a stabilizer and/or blocking agent of human or animal origin.

6. The aqueous solution according to claim 5, wherein the stabilizer and/or blocking agent of human or animal origin is selected from the group consisting of animal sera, skimmed milk, hydrolyzed caseins, non-hydrolyzed caseins, bovine albumin, human albumin, and gelatins.

7. An immunoassay kit comprising the aqueous solution according to claim 3 and at least one binding partner to an analyte to be detected or quantified by immunoassay.

8. An immunoassay method comprising using the composition according to claim 1 as a stabilizer and/or blocking agent for at least one immunoassay reagent.

9. The immunoassay method according to claim 8, wherein the composition reduces non-specific interaction between (i) at least one binding partner intended to detect or quantify an analyte in a biological sample that may contain the analyte and (ii) a solid phase.

10. The immunoassay method according to claim 8, wherein the composition reduces non-specific interaction between (i) an immunoassay positive control, an immunoassay standard and/or an immunoassay adjuster, and (ii) a solid phase.

11. An immunoassay method for determining presence or for quantification of a target analyte in a biological sample that may contain the target analyte, comprising contacting the biological sample with at least two binding partners to the target analyte, P1 and P2, sequentially or simultaneously, wherein:
  one of the two partners P2 is labelled to show the presence of the target analyte if present;
  the labelled partner P2 is contained in the composition according to claim 1 to form a P1/analyte/P2 complex; and
  detection of the presence of the P1/analyte/P2 complex when formed allows conclusions to be drawn concerning presence or quantity of the target analyte in the biological sample.

12. An immunoassay method for determining presence or for quantification of a target analyte in a biological sample that may contain the target analyte, comprising contacting the biological sample with at least one binding partner P1 to the target analyte and a reagent R1 that competes with the target analyte, wherein:
  the reagent R1 is labelled to show indirectly the presence of the target analyte;
  the reagent R1 is contained in the composition according to claim 1 to form a P1/R1 complex; and
  detection of the presence of the P1/R1 complex formed allows conclusions to be drawn indirectly concerning absence or quantity of the target analyte in the biological sample.

* * * * *